(12) United States Patent
Bodduluri

(10) Patent No.: US 7,806,121 B2
(45) Date of Patent: Oct. 5, 2010

(54) FOLLICULAR UNIT TRANSPLANTATION PLANNER AND METHODS OF ITS USE

(75) Inventor: Mohan Bodduluri, Palo Alto, CA (US)

(73) Assignee: Restoration Robotics, Inc., Mountain View, CA (US)

(*) Notice: Subject to any disclaimer, the term of this patent is extended or adjusted under 35 U.S.C. 154(b) by 1024 days.

(21) Appl. No.: 11/539,022

(22) Filed: Oct. 5, 2006

(65) Prior Publication Data

US 2007/0150247 A1 Jun. 28, 2007

Related U.S. Application Data

(60) Provisional application No. 60/753,602, filed on Dec. 22, 2005, provisional application No. 60/764,173, filed on Jan. 31, 2006.

(51) Int. Cl.
*A61B 19/00* (2006.01)
(52) U.S. Cl. .................. 128/897; 606/133; 606/187
(58) Field of Classification Search ............... 128/897, 128/898; 606/133; 703/11
See application file for complete search history.

(56) References Cited

U.S. PATENT DOCUMENTS

| | | | |
|---|---|---|---|
| 4,807,163 A | 2/1989 | Gibbons | |
| 6,445,943 B1 | 9/2002 | Ferre et al. | |
| 6,572,625 B1 | 6/2003 | Rassman | |
| 6,585,746 B2 | 7/2003 | Gildenberg | |
| 7,083,611 B2 | 8/2006 | Lemchen | |
| 7,206,627 B2 | 4/2007 | Abovitz et al. | |
| 2004/0034282 A1 | 2/2004 | Quaid, III | |
| 2004/0197728 A1* | 10/2004 | Abolfathi et al. | 433/24 |
| 2004/0204760 A1* | 10/2004 | Fitz et al. | 623/14.12 |
| 2007/0078466 A1 | 4/2007 | Bodduluri et al. | |
| 2008/0004633 A1 | 1/2008 | Arata et al. | |

FOREIGN PATENT DOCUMENTS

WO 2007/041014 4/2007

OTHER PUBLICATIONS

Robert M. Bernstein, MD; William R. Rassman, MD; Wojciech Szaniawski, MD and Alan J. Halperin, MD. "Follicular Transplantation" Int. Journal of Aesthetic and Restoration Surgery, vol. 3, No. 2, 1995, pp. 119-132.

(Continued)

*Primary Examiner*—Charles A Marmor, II
*Assistant Examiner*—Carrie Dorna
(74) *Attorney, Agent, or Firm*—Lena I. Vinitskaya; Sharon Upham; David T. Burse

(57) ABSTRACT

A system for planning transplantation of follicular units in a body surface of a patient includes a user interface comprising a software-controlled processor, a monitor, and an input device, wherein the system is configured for acquiring images of the body surface, processing the images to produce a three-dimensional model of the body surface, displaying a graphic rendering of the body surface model on the monitor, and displaying on the body surface model a proposed recipient area for implanting follicular units based at least in part on an actual or desired physical characteristic of the patient.

40 Claims, 15 Drawing Sheets

OTHER PUBLICATIONS

Ronald Shapiro, MD. "Principles and techniques used to create a natural hairline in surgical hair restoration", Facial Plast Surg Clin N Am 12 (2004) pp. 201-217.

Rolf Hoffmann and Dominique Van Neste. "Recent Findings with Computerized Methods for Scalp Hair Growth Measurements". J Investig Dermatol Symp Proc 10: pp. 285-288, 2005.

Mohammed Alhaddab, MD; Thomas Kohn, MD; and Mark Sidloi, BSc. Effect of Graft Size, Angle, and Intergraft Distance on Dense Packing in Hair Transplant. Dermatol Surg 2005; 31: pp. 650-654. Published by BC Decker Inc.

Robert M. Bernstein, MD; William R. Rassman, MD. "The Logic of Follicular Unit Transplantation" Dermatologic Clinics. vol. 17, No. 2, Apr. 1999. pp. 277-296.

Francsico Jimenez, MD and Jose M. Ruifernandez, PhD. Distribution of Human Hair in Follicular Units. Dermatologic Surgery 1999; 25: pp. 294-298.

William R. Rassman, MD and Sharon Carson, BA. "Micrografting in Extensive Quantities". http://www.newhair.com/resources/mp-1995-micrografting.asp (7 pages).

Computerworld. "Dispatches & Images from the Fringes of the Electronic Frontier". Mar. 30, 1998, Nexis, p. 1.

PCT International Search Report and Written Opinion for PCT/US07/80646 of the International Search Authority, Applicant Restoration Robotics, Forms PCT/ISA/210, 220 and 237, mailed Sep. 19, 2008 (7 pages).

Riordan, Teresa, "Implanting hair is tedious, exacting work—the perfect work for a robot," The New York Times, Monday, Sep. 15, 2003 (1 page).

"Geometric Design and Fabrication of Developable Bezier and B-Spline Surfaces". R.M.C. Bodduluri and B. Ravani. Transactions of the ASME. vol. 116, Dec. 1994. pp. 1042-1048 (7 pages).

Communication from Australian Patent Office, dated Feb. 11, 2010, in the related Australian application No. 2007303060 of Restoration Robotics, Inc., (2 pages).

\* cited by examiner

FIG. 1.A
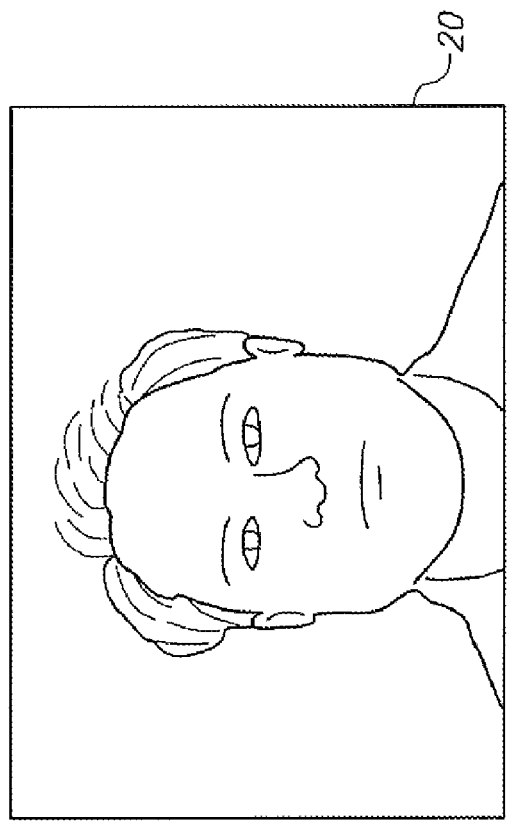
FIG. 1.B

text truncated …

FOLLICULAR UNIT TRANSPLANTATION PLANNER AND METHODS OF ITS USE

RELATED APPLICATION DATA

The present application claims the benefit under 35 U.S.C. §119 to U.S. provisional patent application Ser. Nos. 60/753,602, filed Dec. 22, 2005, and 60/764,173, filed Jan. 31, 2006. These applications, along with U.S. patent application Ser. No. 11/380,907, filed Apr. 28, 2006, are each hereby incorporated by reference into the present application in their entirety.

FIELD OF INVENTION

This invention relates generally to planning systems and their use for planning transplantation (i.e., harvesting and implantation) of hair follicular units in a body surface, usually a scalp.

BACKGROUND

Hair transplantation procedures are well-known, and typically involve (e.g., in a patient having male pattern baldness) harvesting donor hair grafts from the side and back fringe areas ("donor areas") of the patient's scalp, and implanting the harvested follicular units in a bald, top area ("recipient area"). Historically, the harvested grafts were relatively large (3-5 mm), although more recently, the donor grafts may be single follicular units, which are naturally occurring aggregates of 1-3 (and much less commonly, 4-5) closely spaced hair follicles that are distributed randomly over the surface of the scalp.

In one well-known process, a linear portion of the scalp is removed from a donor area using a scalpel cutting down into the fatty subcutaneous tissue. The strip is dissected (under a microscope) into component follicular units, which are then implanted into a recipient area in respective incisions or puncture holes made using a needle. Forceps may be used to grasp and place the individual follicular unit grafts into the needle puncture locations, although other instruments and methods are known for performing this task.

U.S. Pat. No. 6,585,746 discloses a hair transplantation system utilizing a robotic system, including a robotic arm and a hair follicle introducer associated with the robotic arm. A video system is used to produce a three-dimensional image of the patient's scalp, which is used to plan the scalp locations to receive hair grafts implanted by the follicle introducer under the control of the robotic arm.

SUMMARY

In accordance with one aspect of the invention, a method of planning for the transplantation of follicular units in a body surface of a patient includes providing a user interface comprising a software-controlled processor, a monitor, and an input device. The method further includes acquiring images of the body surface, processing the images to produce a three-dimensional model of the body surface, and displaying a graphic rendering of the body surface model on the monitor. A proposed recipient area for implanting follicular units is then displayed on the body surface model, wherein the location of the displayed recipient area may be originally identified, subsequently modified, or both, based at least in part on user input received through the user interface. By way of non-limiting examples, the user input may relate to a density or a type (or a mix of type) of follicular units when implanted in an area of the body surface corresponding to the displayed recipient area. By way of further, non-limiting examples the location of the displayed recipient area may relate to an appearance or direction of hair follicles growing from follicular units when implanted in an area of the body surface corresponding to the displayed recipient area.

The method may further include displaying on the body surface model a graphic rendering of hair follicles growing from follicular units implanted along a boundary of the recipient area, wherein one or both of a location of the recipient area boundary and the displayed hair follicles may be modified based at least in part on input received through the user interface. By way of non-limiting example, the graphic rendering of hair follicles may be based, at least in part, on a user selected relative randomness of implantation locations of follicular units to be implanted along the boundary. The method may further include identifying user-defined recipient areas, or patches, in which follicular units are to be implanted.

The method may further include displaying on the body surface model a donor area for harvesting follicular units, wherein the location of the displayed donor area is based, at least in part, on input received through the user interface. The location of the displayed donor area may alternatively or additionally be based on one or more of (i) an amount of each of a type of existing follicular unit located in a donor area on the actual body surface corresponding to the displayed donor area, as determined from the acquired images, (ii) a minimum density of follicular units to be left remaining in the donor area after selected harvesting of other follicular units has occurred, and (iii) an approximate amount of each type, color, or both, of existing follicular unit to be implanted in an area of the body surface corresponding to the displayed recipient area.

In some embodiments, the method further comprises identifying locations of follicular units to be harvested from an area on the body surface corresponding to the displayed donor area, identifying locations of implantation sites on the body surface corresponding to the displayed recipient area at which the harvested follicular units are to be implanted, and providing the respective harvest and implantation locations to an automated (e.g., robotic) system for performing the implantation procedure.

In accordance with another embodiment of the invention, a system for planning for the transplantation of follicular units in a body surface of a patient includes a user interface comprising a software-controlled processor, a monitor, and an input device. The system is configured to acquire and process images of the body surface to generate and display on the monitor a three-dimensional model of the body surface. The planning system is further configured to display a proposed recipient area for implanting follicular units on the body surface model, wherein the location of the displayed recipient area may be originally identified, subsequently modified, or both, based at least in part on user input received through the user interface. By way of non-limiting examples, the user input may relate to a density or a type (or a mix of type) of follicular units when implanted in an area of the body surface corresponding to the displayed recipient area. By way of further, non-limiting examples the location of the displayed recipient area may relate to an appearance or direction of hair follicles growing from follicular units when implanted in an area of the body surface corresponding to the displayed recipient area.

The planning system may be further configured to display on the body surface model a graphic rendering of hair follicles growing from follicular units implanted along a boundary of the recipient area, wherein one or both of a location of the recipient area boundary and the displayed hair follicles may be modified based at least in part on input received through the user interface. By way of non-limiting example, the graphic rendering of hair follicles may be based, at least in part, on a user selected relative randomness of implantation locations of follicular units to be implanted along the boundary. The system may also be configured to identify user-defined recipient areas, or patches, in which follicular units are to be implanted.

The planning system may be further configured to display on the body surface model a donor area for harvesting follicular units, wherein the location of the displayed donor area is based, at least in part, on input received through the user interface. The location of the displayed donor area may alternatively or additionally be based on one or more of (i) an amount of each of a type of existing follicular unit located in a donor area on the actual body surface corresponding to the displayed donor area, as determined from the acquired images, (ii) a minimum density of follicular units to be left remaining in the donor area after selected harvesting of other follicular units has occurred, and (iii) an approximate amount of each type, color, or both, of existing follicular unit to be implanted in an area of the body surface corresponding to the displayed recipient area.

In some embodiments, the planning system identifies locations of follicular units to be harvested from an area on the body surface corresponding to the displayed donor area, and of implantation sites on the body surface corresponding to the displayed recipient area at which the harvested follicular units are to be implanted, and inputs the respective harvest and implantation locations into an automated (e.g., robotic) system for performing the implantation procedure.

Other and further embodiments, objects and advantages of the invention will become apparent from the following detailed description when read in view of the accompanying figures.

BRIEF DESCRIPTION OF THE DRAWINGS

Embodiments of the invention are illustrated by way of example and not limitation in the figures of the accompanying drawings, in which like references indicate similar elements, and in which:

FIGS. 1A and 1B are images (pictures) of a front and side profile of a patient's head.

DETAILED DESCRIPTION

Figure 2:
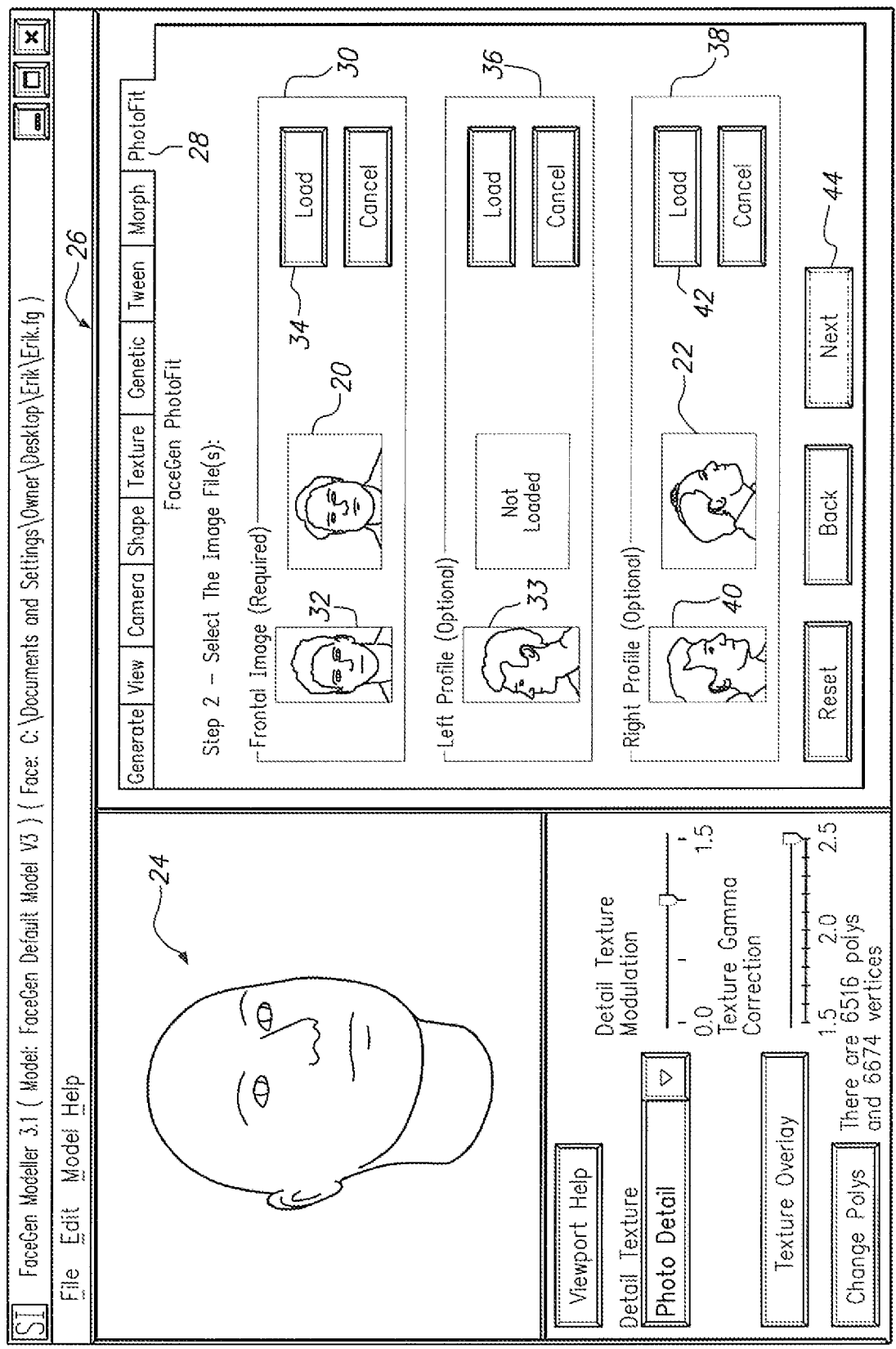
FIGS. 2-6 are respective monitor screen shots of a user interface generated by modeling software used for creating a three-dimensional surface model of the patient's head based on the acquired images, in accordance with one embodiment.

The above-incorporated U.S. Provisional Patent Application Ser. Nos. 60/753,602 and 60/764,173 (hereinafter collectively, "Bodduluri et al") disclose various embodiments of an automated system, in particular an image-guided robotic system, and methods of its use for performing follicular unit harvesting and implantation (transplantation) procedures in a body surface, typically a human scalp. After the robotic system has been initiated and calibrated, image data of the body surface is acquired and processed by the system computer to identify objects, in particular follicular units in a donor region on a human scalp. From images of this region of interest, image segmentation and screening software residing in the computer identifies and selects particular follicular units of interest for harvesting from the scalp.

As described in Bodduluri et al, the aesthetic result of a hair transplantation procedure depends in part on implanting the grafts in natural-looking patterns. A computer can efficiently "amplify" a surgeon's skill by "filling in the blanks" among a small fraction of the implant sites for which the surgeon determines graft location and orientation. Achieving a natural-looking hairline is particularly important for a good aesthetic result. Instead of painstakingly making incisions for all of the near-hairline implant sites, the surgeon indicates a few hairline implant locations and orientations and the computer fills in the rest by interpolating among the designated sites, using the imaging system to identify and avoid existing follicular units.

Bodduluri et al illustrates an algorithm using control points to design natural looking hairline. A curve is designed using control points based on, for example, b-spline cubic polynomials. The control points are specified by the operator. The orientation of the hair at each of the control points is specified. Points along the curve are identified at a given spacing, for instance, by interpolation. The locations of the points along the curve may be randomized to make a natural looking hair line. The amount of randomization may be user-specified or computer-generated. It is preferable that the follicular unit orientations are not randomized but are interpolated, for example, the same way a cubic spline is generated. Randomization of the location and interpolation of the orientation create more natural looking implants.

Natural looking randomness is important in both the critical hairline region and in the balance of the recipient sites. This can be achieved using a procedure illustrated in Bodduluri et al, wherein a surface is designed using control points based on, for example, b-spline cubic surfaces. Again, the orientation of the hair at each of the control points is specified. Implant points along the surface are identified at a given spacing. The locations of the points along the surface may be randomized to make a natural looking hair distribution. The amount of randomization may be user-specified or computer-generated. Again, the orientation of the respective follicular units is preferably not randomized, but interpolated the same way a cubic spline surface is generated. Randomization and interpolation schemes are known in the art, and can be adapted for this method.

Bodduluri et al shows an example of an automatic guidance feature of the robotic system, including the step of planning implant locations and orientations with respect to global landmarks (e.g., existing hairs, tattoos, or other distinguishing features). The robot is then moved to register landmarks on the patient. The register information can be stored in memory for reference. The robot can make use of the registered landmarks as reference points for recognizing its position relative to the working surface. The robot is moved to each of the implant location and orientation with respect to the global landmarks. The global landmarks provide a global reference for global movements. The location and orientation are fine-tuned based on the nearby landmarks such as neighboring preexisting hairs or newly implanted hairs. The nearby landmarks provide a local reference for local movements.

Next, a treatment plan is input into the computer. For example, the treatment plan is a prescribed plan designed to transplant hair follicles from a first region (harvest region) to a target region (implant region). In such cases, the treatment plan may include one or more parameters, such as a number of hair follicles to be removed/implanted, location of harvest region, location of implant region, a degree of randomness associated with targeted implant locations, spacing between adjacent targeted implant locations, depth of follicle, depth of implant, patient identification, geometric profile of harvest region, geometric profile of implant region, marker location (s), and density of targeted implant locations.

Various techniques may be used to input the treatment plan into the computer. In the illustrated embodiments in Bodduluri et al, the treatment plan may be inputted using a user interface that includes a monitor and a keyboard. Alternatively, the treatment plan may be inputted using a storage device, such as a diskette or a compact disk. In other embodiments, the treatment plan may be downloaded from a remote server, or from a combination of the forgoing techniques. For example, some parameters may be inputted into the computer using a diskette, while other parameters may be inputted using the user interface. In some embodiments, one or more parameters of the treatment plan may be determined in real time (e.g., during a treatment session).

After the treatment plan has been input into the computer, the computer then registers the treatment plan with a patient. In some embodiments, such may be accomplished by using one or more cameras to identify one or more markers on the patient. The marker may be a reflector that is secured to the patient, an ink mark drawn on the patient, or an anatomy of the patient. The identified marker(s) may be used to determine a position and/or orientation of a target region on the patient.

In accordance with various embodiments of the invention, a system for planning a procedure for the transplantation of follicular units in a body surface (e.g., a scalp) of a patient comprises a user interface, including a software-controlled processor, a monitor, and an input device. These components are common to virtually all modern computer systems, whether a stand alone (e.g., "personal") computer system, or in a system employing a centralized server with multiple remote terminal(s). It will be appreciated that embodiments of the planning system are preferably (if not exclusively from a practical point of view) software implemented, and may be run on any computer system having the basic components (processor, monitor, input device), so long as such computer system is equipped with sufficient available memory and an appropriate graphic generation and display capability.

It will also be appreciated that embodiments of the invention may be implemented over the internet, e.g., with a user of such system employing his or her home computer as at least a part of the user interface (monitor and input device) that interacts with a remote server or computer. In such an internet-based planning system, the software that implements and controls the user interface may reside in whole or part on the user's computer or on the remote server/computer, preferably transparent to the user. In one such embodiment, the remote server downloads one or more software modules to the user's computer for temporary or permanent use.

Exemplary embodiments of a software implemented and controlled user interface for planning a follicular unit transplantation procedure will now be described in conjunction with the accompanying figures. It will be appreciated that various and multiple variations of the described embodiments may be implemented without departing from the general scope of the invention, which is set forth in the appended claims.

With reference to FIGS. 1A and 1B, images are acquired of a body surface of a patient, in this case, a front view 20 (FIG. 1A) and a side view 22 (FIG. 1B) of the patient's head (and, in particular, scalp), for which the subject transplantation procedure is being planned. By way of non-limiting example, the images 20, 22 may be acquired using a hand held digital camera, and input through the user interface of the planning system, in accordance with well-known and available technology for transmitting digital image data. It is not necessary in preferred embodiments to include images of every portion of the patient's head, since the modeling software (described below in greater detail) can generate a sufficiently accurate three-dimensional surface model of the head/scalp from just front and side views 20 and 22, respectively.

With reference generally to FIGS. 2-6, the acquired images 20, 22 are then processed to generate a three-dimensional model of the patient's head (scalp) using commercially available modeling software. In the illustrated embodiment, Face-Gen Modeller 3.1 produced and distributed by Singular Inversions, Inc., Vancouver, Canada is used to generate the three-dimensional model. It will be appreciated that other software programs may alternatively be used.

With more specific reference to FIG. 2, a monitor screen shot from the user interface taken during use of the FaceGen Modeller program includes a series of pull-down menus 26 related to construction of a model of a human face. The menu "PhotoFit" 28 has been selected, resulting in the display of a frontal image 30 (in this case, image 20), a left profile image 36 (an optional input; in this case, not provided) and a right profile image 38 (also optional; in this case, side image 22) of the patient. The software program displays respective front 32, left profile 33, and right profile 40 images of a model as an example for users of the system. Once the images 20 and 22 are loaded into the modeling software (via user-interface menu inputs 34 and 42), a subsequent screen shot menu is provided (i.e., after "clicking" on the "next" menu field item 44).

Figure 3:
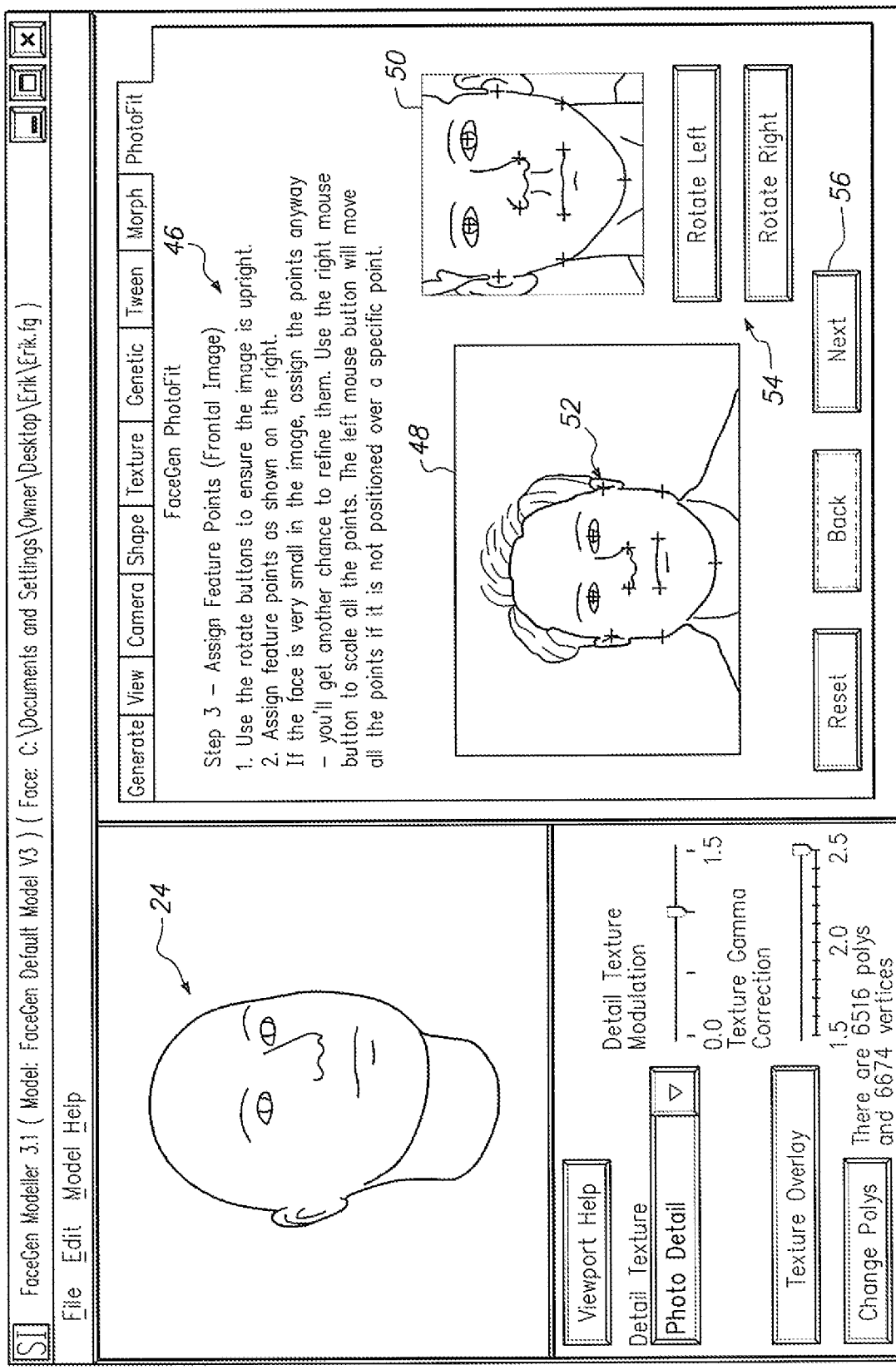
Figure 4:
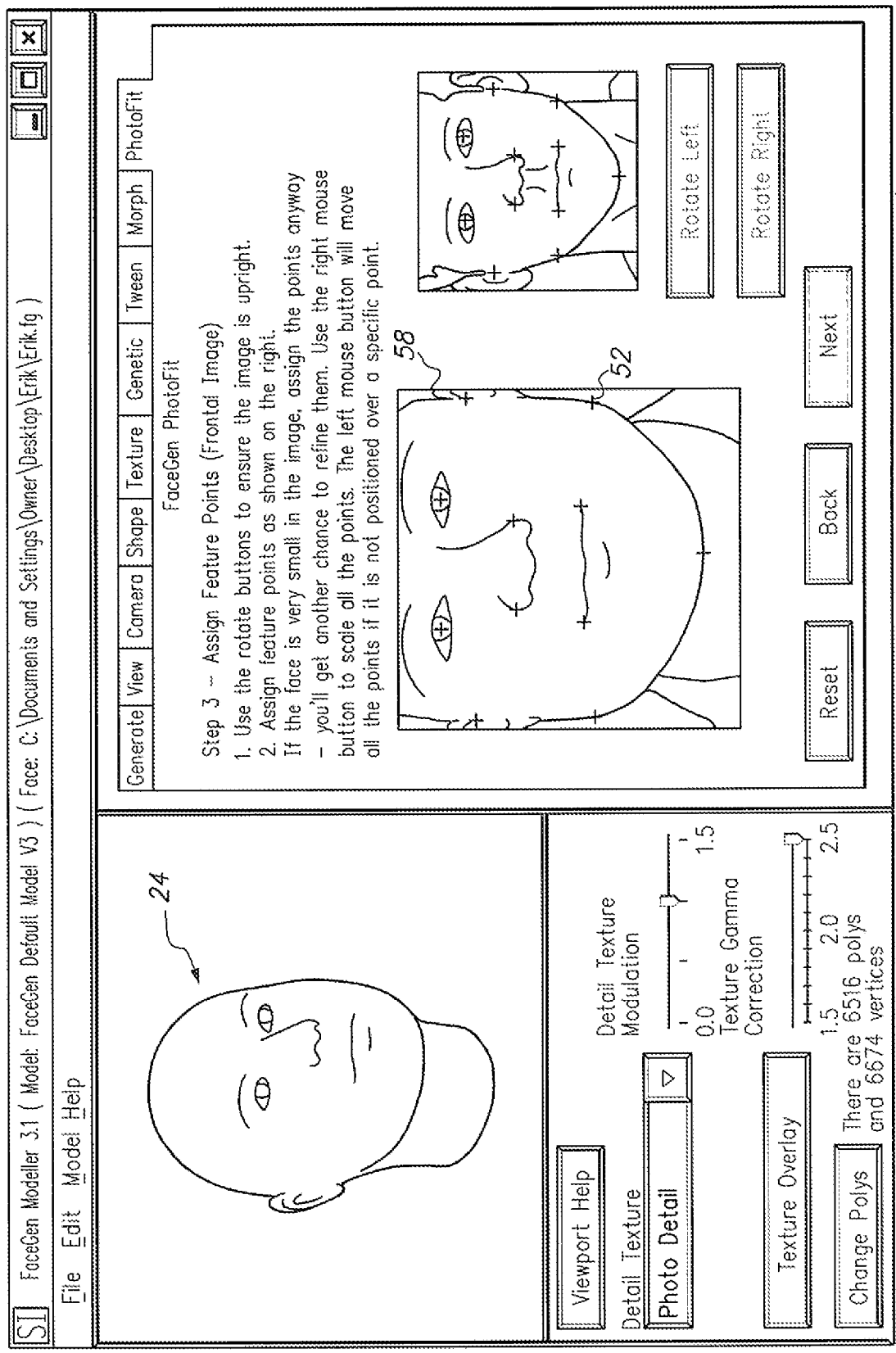
Figure 5:
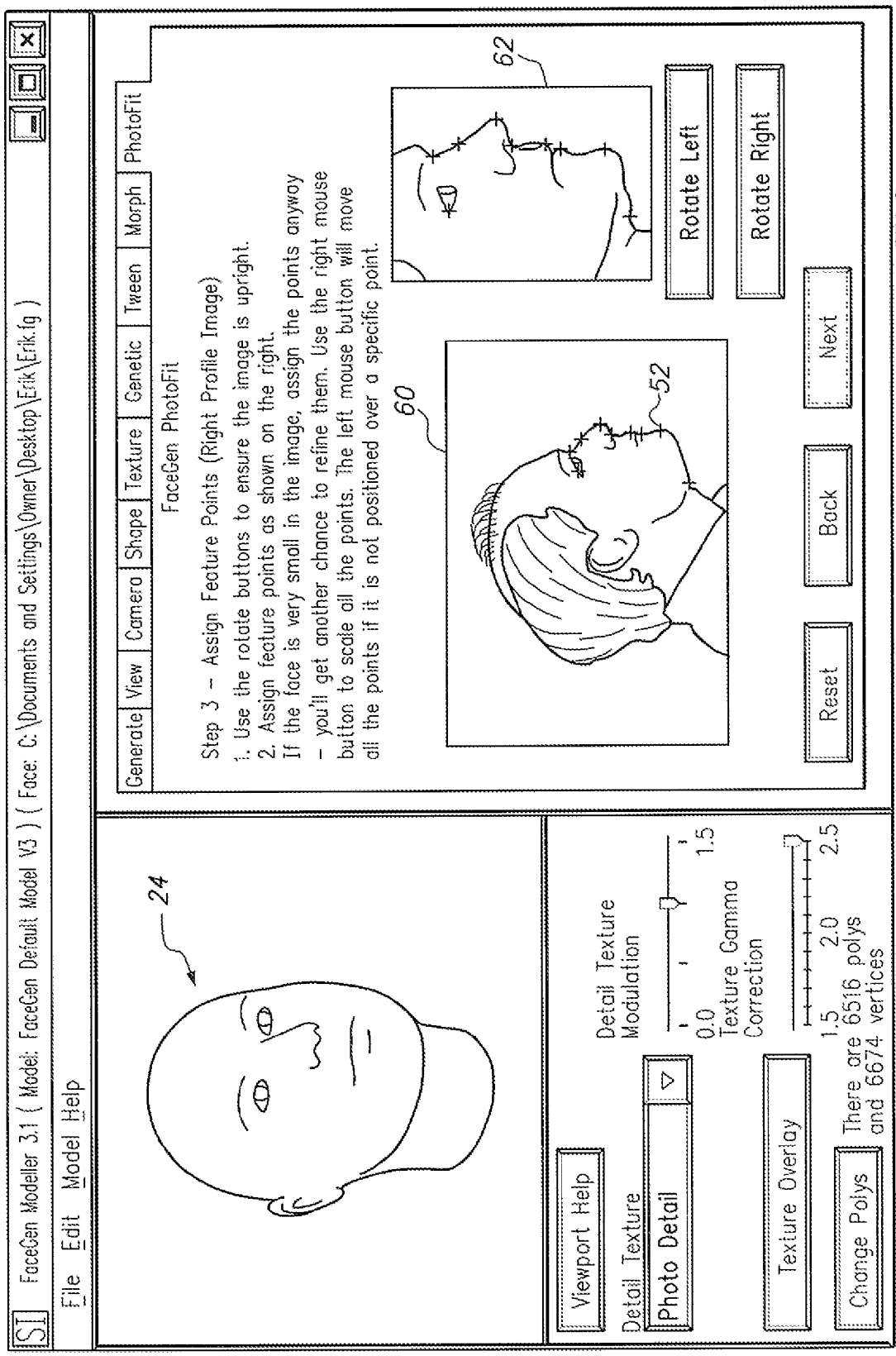
Figure 6:
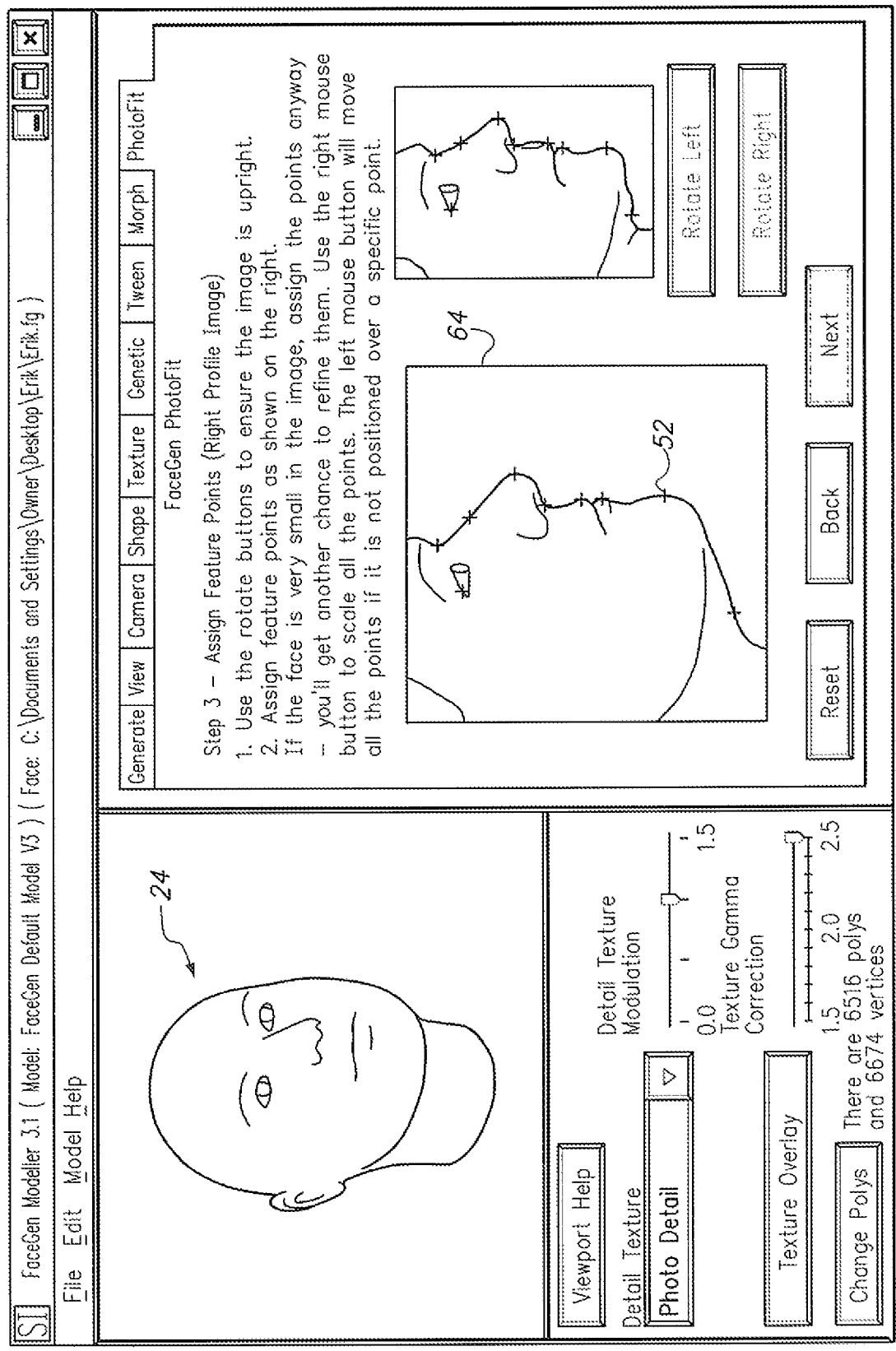

Referring to field 46 in FIG. 3, in order to generate a three-dimensional model of the patient's head/scalp, the user assigns a series of feature points 52 on the frontal image 20 (designated by reference numeral 48), based on the provided example 50. In brief, the feature points 52 are placed at distinct physical locations (e.g., corners of the mouth, nose, chin, ears, etc.) of the patient's face. The image 48 may be rotated using the respective inputs 54. As shown in FIG. 4, the modeling software allows the user to enlarge the frontal image (designated by reference number 58) for accurate placement of the feature points 52. Referring to FIGS. 5 and 6, the process is repeated for assigning feature points to the side profile image(s), in this case to the right profile image 60 in FIG. 5, and enlarged 64 in FIG. 6), with an example model picture 62 provided for illustration. Further information regarding generation of a three-dimensional model based on the acquired front and side images may be ascertained directly from the FaceGen Modeller software.

Figure 7:
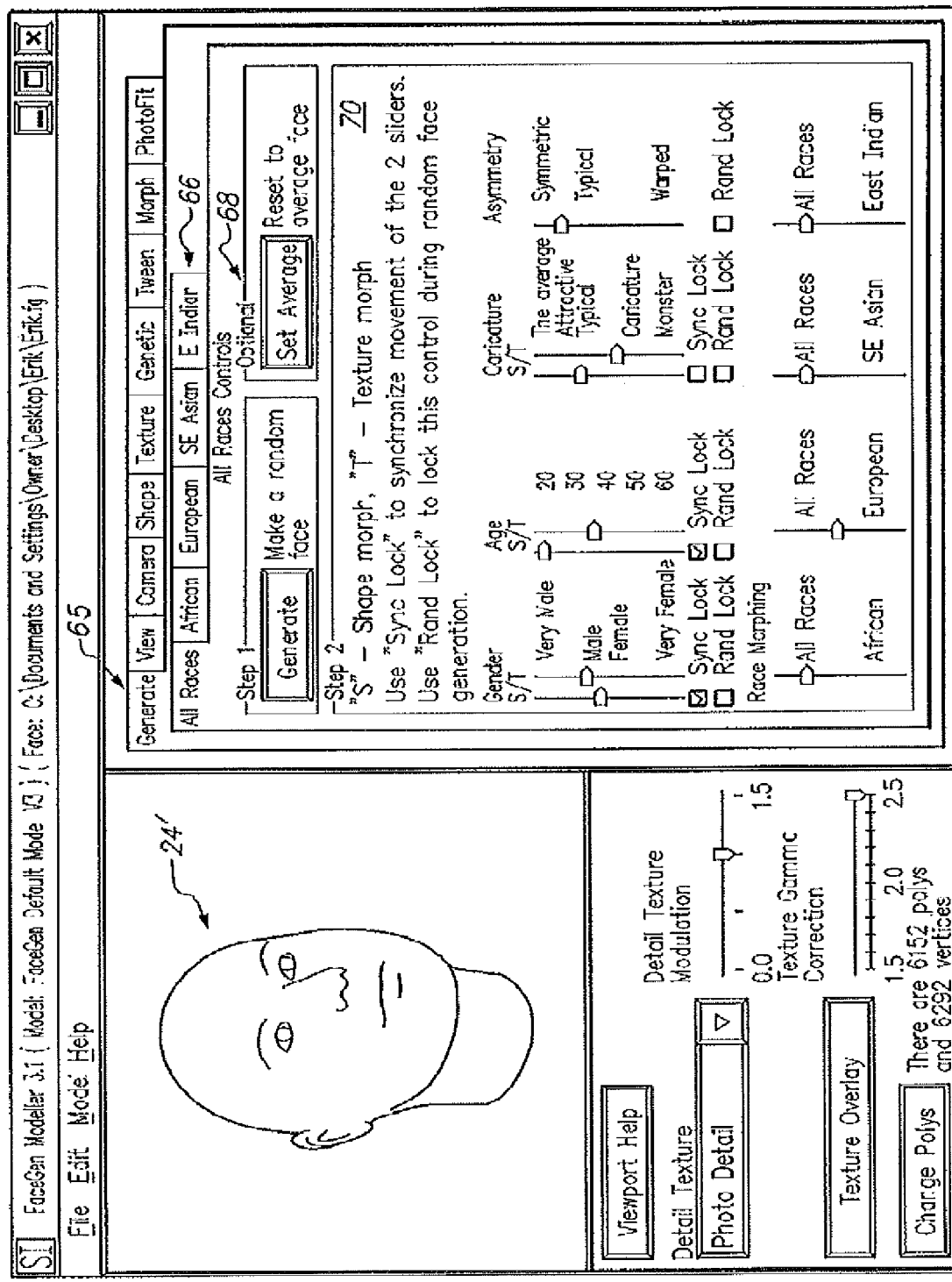
FIG. 7 is a further monitor screen shot of a user interface generated by the modeling software for creating a three-dimensional model based on selected appearance input parameters instead of acquired images.

With reference to FIG. 7, in an alternate embodiment in which acquired images of the patient's head/scalp (or other applicable body surface) are not provided, the modeling software is configured to generate (by selecting menu option "generate" 65) a three-dimensional model (designated as 24') based on inputs relating to selected characteristics, such as race 66 and other characteristics selected through menus 68 and 70, some objective (e.g., gender, age) and others purely subjective (e.g., attractive).

In some embodiments, further input information is provided to the planning system in addition to generating the body surface model. For example, particular features specific to hair follicles (e.g., color or coarseness) may be derived from the images and/or input through the user interface. Further information may be either user input or determined from the acquired images using image processing, such as geometric shape of the body surface (e.g., patient's head), existing hair lines, and a number of each type (i.e., single or multiple follicle) and color (e.g., dark, light, gray, etc.) of follicular unit that are available for harvesting. It will be appreciated that the three dimensional model can alternatively be generated by a number of other methods, for example, using a 3D laser scanner and/or by stiching multiple digital images together. The system of embodiments of the present invention will use the three dimensional information in the same way, without regard to how it is generated.

Figure 8A:
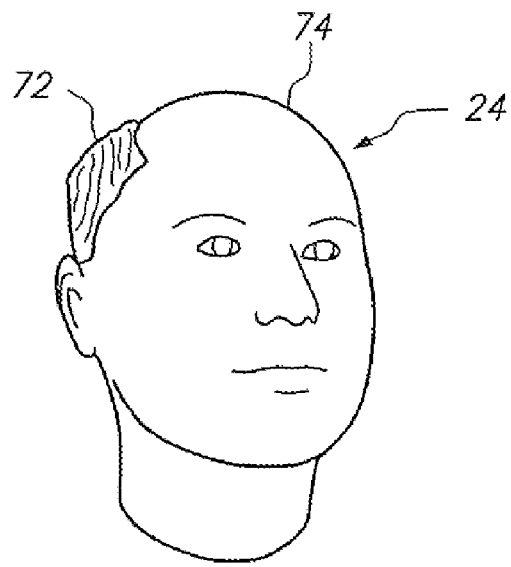
FIGS. 8A and 8B are respective front and back perspective views depicting a completed three-dimensional surface model of the patient's head based on the acquired images.
Figure 8B:
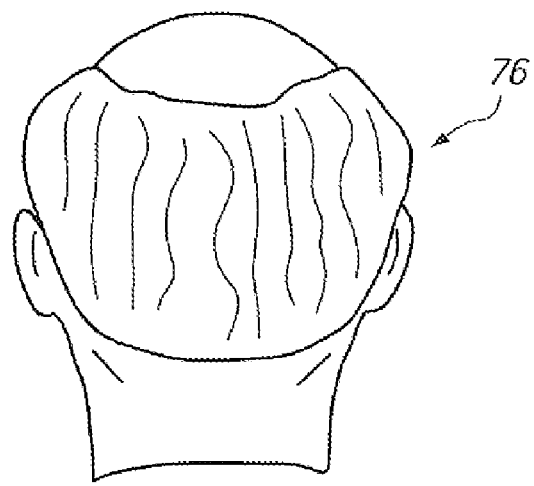

Referring to FIGS. 8A and 8B, whether from the acquired images, or through other descriptive feature inputs, the modeling software generates and displays on the user interface monitor of the planning system a three-dimensional model 24 of the patient's head/scalp. For purposes of illustration, the model generated in FIGS. 8A and 8B exhibits characteristic male-pattern baldness, including a bald top region 74, and populated side 72 and back 76 regions.

Figure 9:
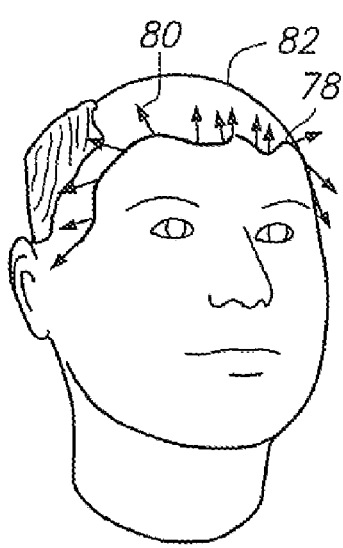
FIG. 9 depicts a proposed front hair line boundary overlaying the body surface model of FIGS. 8A and 8B.
Figure 10:
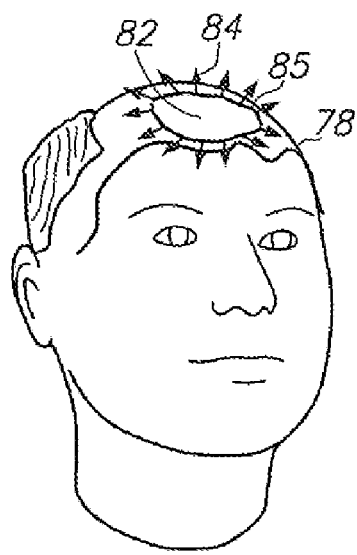
FIG. 10 depicts a proposed hair patch area overlaying the body surface model of FIGS. 8A and 8B.

Referring to FIGS. 9 and 10, based on one or more physical features and information determined from processing the acquired images 20 and 22, and user inputs entered through the user interface, the planning system will display on the body surface model one or more proposed recipient areas 82 for implanting follicular units. An initial location of a proposed front boundary (or "hair line") 78 may be initially identified by the system, or generated based (at least in part) on user input received through the user interface. In either case, it may be modified by the user, as indicated by the arrows 80 e.g., by using a convention click and drag motion of a computer mouse, until the hair line 78 is in a desired location. Once the hair line 78 is established, one or more separate regions (or "patches") 85 behind the hair line may also be initially identified by the system, or generated based (at least in part) on user input received through the user interface. As with the hair line 78, the boundaries of the patches 85 may be modified by the user, as indicated by the arrows 84.

By way of non-limiting examples, input received through the user interface for establishing or modifying the hair line and inner patch boundaries may relate to one or more of a resulting density of the follicular units after they are implanted in the recipient area, a direction of hair follicles that will grow out from the implanted follicular units, and an overall appearance (i.e., hair style) of the hair follicles growing out from the implanted follicular units. Other factors, such as a geometric shape of the body surface, an ethnicity of the patient, an age of the patient, a gender of the patient, and/or existing hair lines, densities and follicle color(s) on the body surface. One or more parameters relating to existing follicular units in an identified donor area of the body surface may also be considered, such as an amount of each type (e.g., single or multiple follicle), color, and a relative coarseness of hair follicles growing from the existing follicular units.

In embodiments of the invention, the attending physician or operator can specify where a follicular unit needs to be implanted and at what angle, i.e., its relative location (or "implantation site"), orientation, and depth. This specification of the location, orientation and/or depth of a hair follicle to be implanted may be carried out by a treatment planning system. Alternatively, during the implanting mode, when the camera(s) are viewing the recipient area of the scalp, the attending operator may use a user interface (e.g., a conventional computer mouse) to specify the implant location and/or position and/or orientation and/or implant depth. Alternatively, the operator can point to location on the scalp by placing a temporary fiducial, such as an ink mark or a pointer that can be visualized, identified, and measured by the image processing system. Further, orientation can be specified directly on the computer monitor as a combination of two angles, such as rotation about x-axis and a rotation about y-axis (assuming that z-axis is along the needle), or by placing an elongated pointer on the scalp, which the image processing system can visualize and measure the angles.

In particular, the available quantity of single follicle follicular units available for harvesting may also play a role in defining the hair line of the recipient area, since the single follicle type of unit is predominantly found in natural front hair lines. U.S. patent application Ser. No. 11/467,283, filed Aug. 25, 2006, [which is fully incorporated herein by reference,] discloses a method for determining an approximate quantity of each type of existing follicular units that are available for harvesting based on processing images of the potential donor area(s). While such donor area(s) are typically in the back of the scalp, the sides may also be a desirable source of donor follicular units, especially where lighter or gray follicular units are needed, since hair follicles on the sides of the head tend to gray faster than those in the back.

Figure 11:
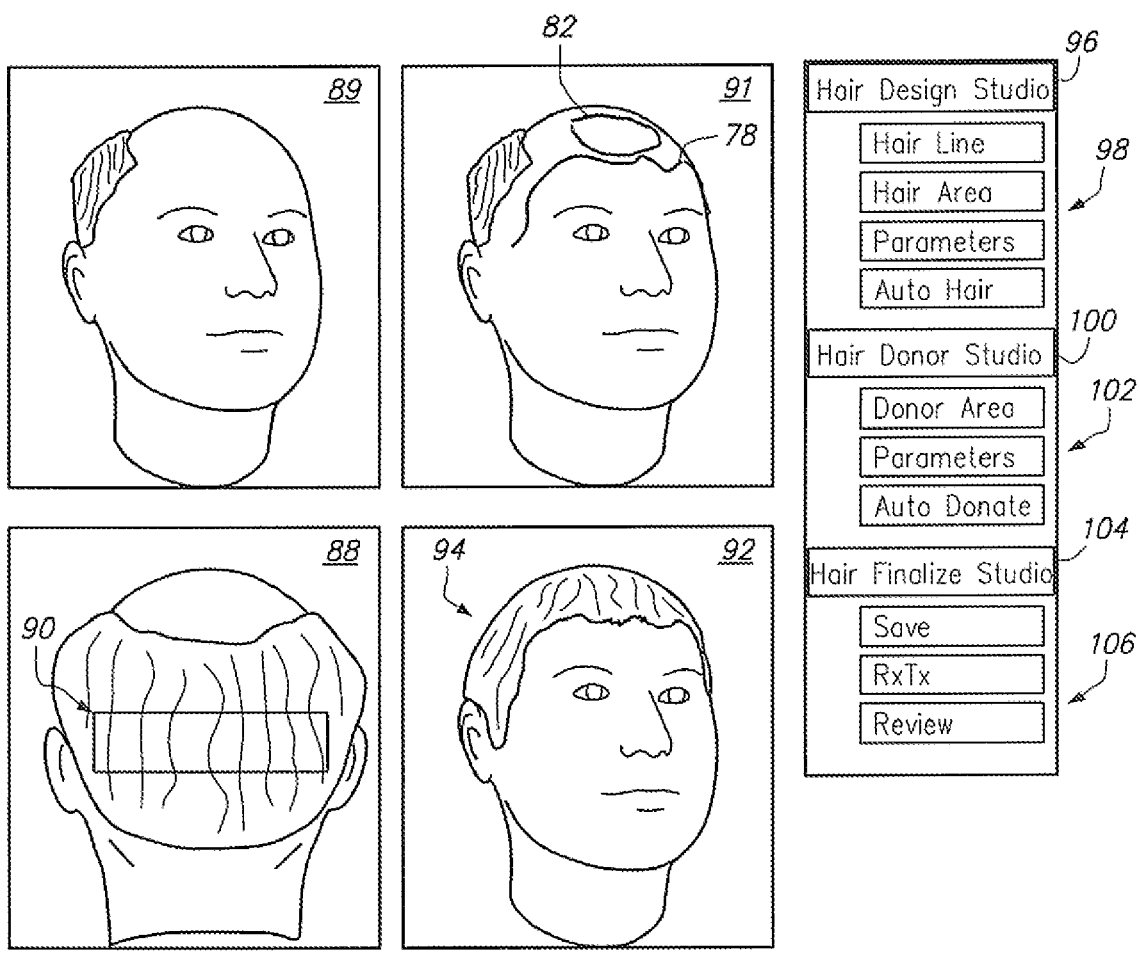
FIG. 11 is a monitor screen shot of a user interface generated by a planning model constructed according to one embodiment.

Referring to FIG. 11, in one embodiment, the user-interface of the planning system may generate and display input menus for the user during a planning process. Such menus may includes, but are not limited to a hair design studio 96, hair donor studio 100 and hair finalize studio 104. The hair design studio 96 may comprise, by way of non-limiting example, an input menu 98 for receiving user inputs relating to specific hair line and hair patch (or "hair area") planning for the recipient area(s), along with related input parameters, and an automatic ("auto hair") feature in which case the hair line and patch areas are identified, preferably including specific implantation locations, by the system without needing further user input.

The hair donor studio 100 may comprise, by way of non-limiting example, an input menu 102 for receiving user inputs relating to a proposed donor area 90, including related parameters and an automatic ("auto donate") feature in which case the donor area is identified by the system without needing further user input. The hair finalize studio 104 may comprise, by way of non-limiting example, an input menu 106 for receiving user instructions relating to saving, transmitting, receiving, reviewing, etc., a completed or partially completed transplantation procedure plan. The display in FIG. 11 also includes a four-way split screen of images, including a first image 89 of the initial patient head model, a second image 91 of the head model during the hair line and patch planning process, a third image 88 of the donor planning process (including a currently identified donor region 90), and a fourth image 92 of a graphic representation of the patient, post-transplantation 94 (i.e., with an artistic rendering of the resulting hair style of the patient).

A person's hair line is formed by the respective locations at which hair follicles emerge from the scalp, as well as the direction(s) relative to the surface of the scalp at which the hair follicles emerge, along the boundary line(s) of the region(s) which have existing or planned (implanted) hair follicular units. Thus, designing a suitable "hair line" curve is a crucial part of achieving a desired, resulting appearance from a hair follicular unit transplantation procedure. In accordance with embodiments of invention, the respective location and direction of the follicular units to be implanted along the hair line boundary is preferably specified along a curve, in order to complete the design of the hair line. This "hair line curve" can be designed in a similar manner as designing a curve in the field of computer aided design, for example, using a well-known technique called a "Bezier representation," or modifications thereof. A Bezier representation is a way of designing arbitrarily-shaped curves based on a specified number of "control points" that will define the curve.

Figure 17:
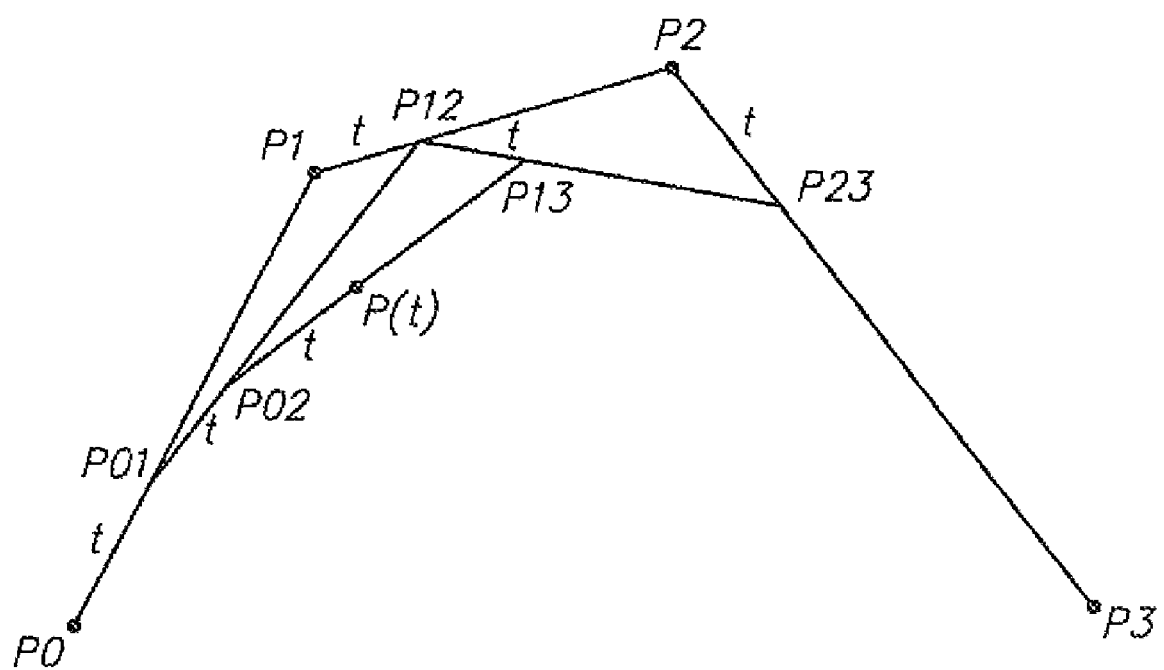
FIG. 17 illustrates a technique used to design arbitrary shaped curves based on user-specified control points (e.g., for planning a front hair-line boundary), in accordance with one embodiment.

By way of example, with reference to FIG. 17, given four control points, $P_0$, $P_1$, $P_2$, $P_3$, a curve function P(t) may be specified, where t is a parameter that varies from 0 to 1. The point on the curve may be calculated analytically, or may be obtained using a graphical construction technique, known as de Casteljau's construction. The steps of the curve construction are as follows:

(1) First, the line segment $P_0P_1$ is subdivided into two parts, based on the relationship, $P_0P_{01}$: $P_{01}P_1$ is t: (1−t). That is, find the point $P_{01}$ that subdivides the line segment $P_0P_1$ into subparts t and (1−t).

(2) Similarly, find the point $P_{12}$ on the line segment $P_1P_2$ and point $P_{23}$ on the line segment $P_2P_3$.

(3) Similarly, find the point $P_{02}$ on the line segment $P_{01}P_{12}$ and the point $P_{13}$ on the line segment $P_{12}P_{23}$.

(4) Finally, find the point P(t) that subdivides, in the same fashion, the line segment $P_{02}P_{13}$.

As may be observed in FIG. 17, as t varies from 0 to 1, a curve is established that extends from $P_0$ to $P_3$, that is, P(0)=$P_0$ and P(1)=$P_3$. Moreover, the line $P_0P_1$ is tangential to the curve at $P_0$ and the line $P_2P_3$ is tangential to the curve at P(3).

Thus, given two points, $P_0$ and $P_1$, finding every point P(t) on the line segment that extends from $P_0$ to $P_1$ is called linear interpolation, given by the expression P(t)=(1−t) $P_0$+t $P_1$. Note that when t=0, P(t)=$P_0$ and when t=1, P(t)=$P_1$. In the (so-called) subdividing each of the line segments described in the above construction, finding a point that subdivides the line segment given t is the same as finding the point on the line segment that corresponds to t by the linear interpolation formula. This construction (or linear interpolation idea) works nicely with an arbitrary specification of the control points $P_0$ through $P_3$ in a plane, where the resulting curve remains in the plane. The construction also works well where one specifies the control points in three dimensions. However, if the four points are specified on a curved surface, the resulting curve does not necessarily stay on the curved surface. That is, if one specifies all the control points on a sphere, then the resulting curve constructed using the above technique does not keep the curve on the sphere.

Thus, embodiments of the planning system according to the present invention preferably employ a modified construction, which keeps the curve on the surface of the planning sphere. Consider two points $P_0$ and $P_1$ lying on a unit sphere, with a center C. The three points together form a plane, and the plane intersects the sphere in a great circle. The two radii $CP_0$ and $CP_1$ subtend an angle theta. Every point on the curve between the two points $P_0$ and $P_1$ can now be parameterized by P(t) such that $P_0$P(t) form an angle theta, and P(t)$P_1$ form an angle (1−t) theta, at the center C. This interpolation scheme is called spherical linear interpolation, in which the resulting curve P(t) goes from $P_0$ to $P_1$ as t varies from 0 to 1. Thus, given four points on a sphere $P_0$, $P_1$, $P_2$, and $P_3$, a Bezier curve can be designed that lies on the sphere similar to the planar construction described earlier, except the linear subdivision (linear interpolation) is replaced by angular subdivision (spherical linear interpolation).

It will be appreciated that an advantage of using control points is that a few user-input points may represent an otherwise complicated set of points forming the hair line curve. Thus, in designing a hair line curve, the user needs to only adjust the control points interactively until the resulting curve is the desired curve that the user is seeking. In a Bezier formulation, the curve passes through the first and the last control points but not the middle ones. The middle control points specify the slope of the curve at the beginning of the curve and at the end of the curve. Specifying points on the curve and the slopes of the curve may not be intuitive to the user, and it may be preferable to instead specify control points that lie on the curve. Such a formulation exists, and it is called Cardinal spline.

In the case of a Cardinal spline, a set of control points $P_0$, $P_1 \ldots P_n$ are specified on the curve. For a pair of the control points Pi and Pi+1, the Bezier control points are as follows: $B_0$=Pi; $B_3$=Pi+1. $B_1$ is chosen such that the respective slope of the curve at $B_0$ is defined by Pi+1 and Pi−1, $B_2$ is chosen such that the slope of the curve at $B_3$ is defined by Pi+2 and Pi. The length of the tangent can be adjusted to alter the behavior of the curve. A Catmull ROM Spline is a special case of cardinal spline, wherein a specific length of the tangent is used in calculating $B_1$ and $B_2$. Using these four control points, a Bezier curve can be calculated that goes through Pi−1 and Pi, as per the Bezier formulation described earlier. The Cardinal spline formulation guarantees that the curve passes through all the control points. This curve on the sphere can be projected on to the surface of the patient's 3D body surface (head/scalp) model to design the desired hair line for the patient.

Figure 12:
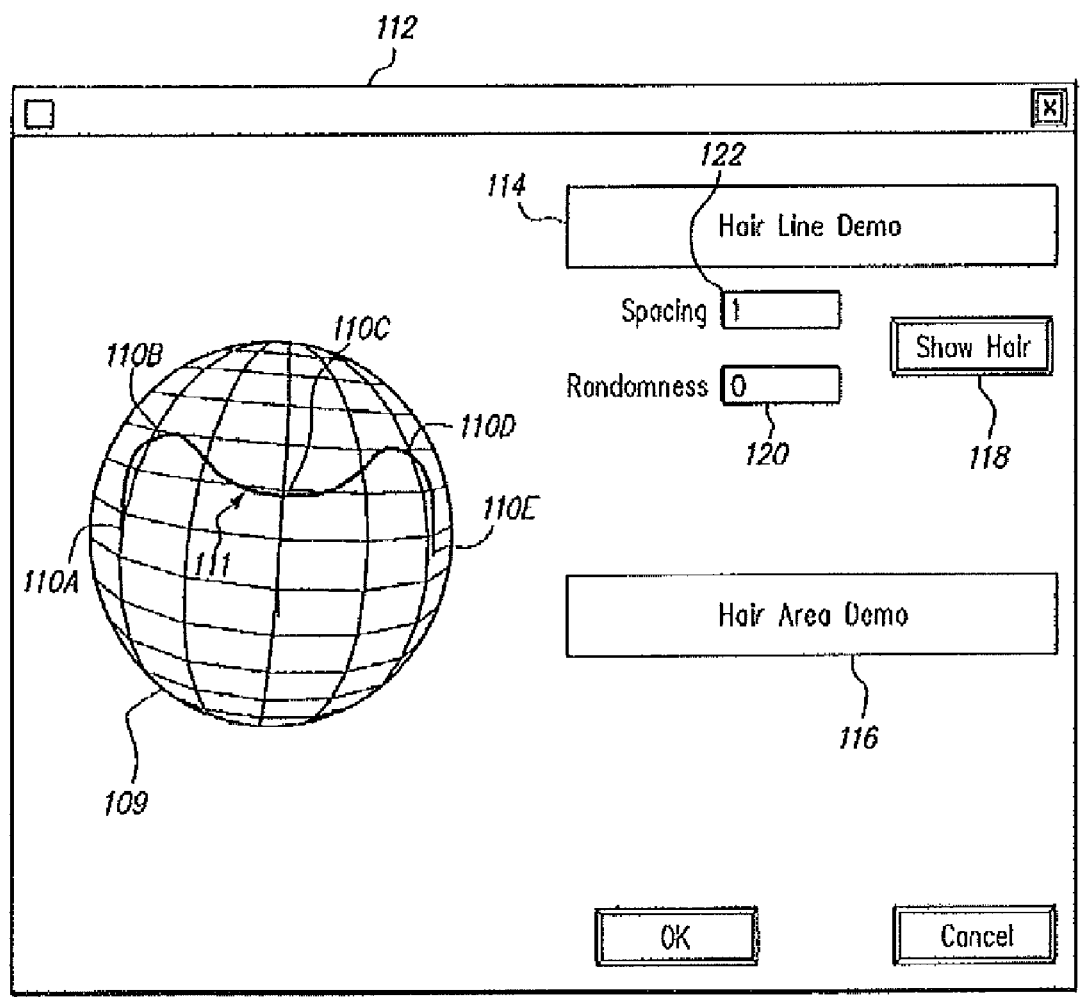
FIG. 12 is another monitor screen shot generated by a planning model constructed according to one embodiment, depicting a rudimentary hair line design employing a plurality of control points.

One embodiment of a hair transplantation planning system of the present invention that employs the above-described modified Bezier representation for hair line curve construction is depicted in FIG. 12, in which five control points (or "control hairs") 110A-110E have been specified by a user through a user interface 112 to define an initial hair line curve 111 on a spherical modeling surface 109. The user interface 112 allows the user to select a hair line demonstration (or demo) 114 or a hair area demonstration (demo) 116. In the illustrated embodiments, the hair line demo 114 has been selected, which allows for additional user inputs including specifying a density, or spacing 122 (in mm) between implantation locations, and a "randomness" factor 120.

Figure 13:
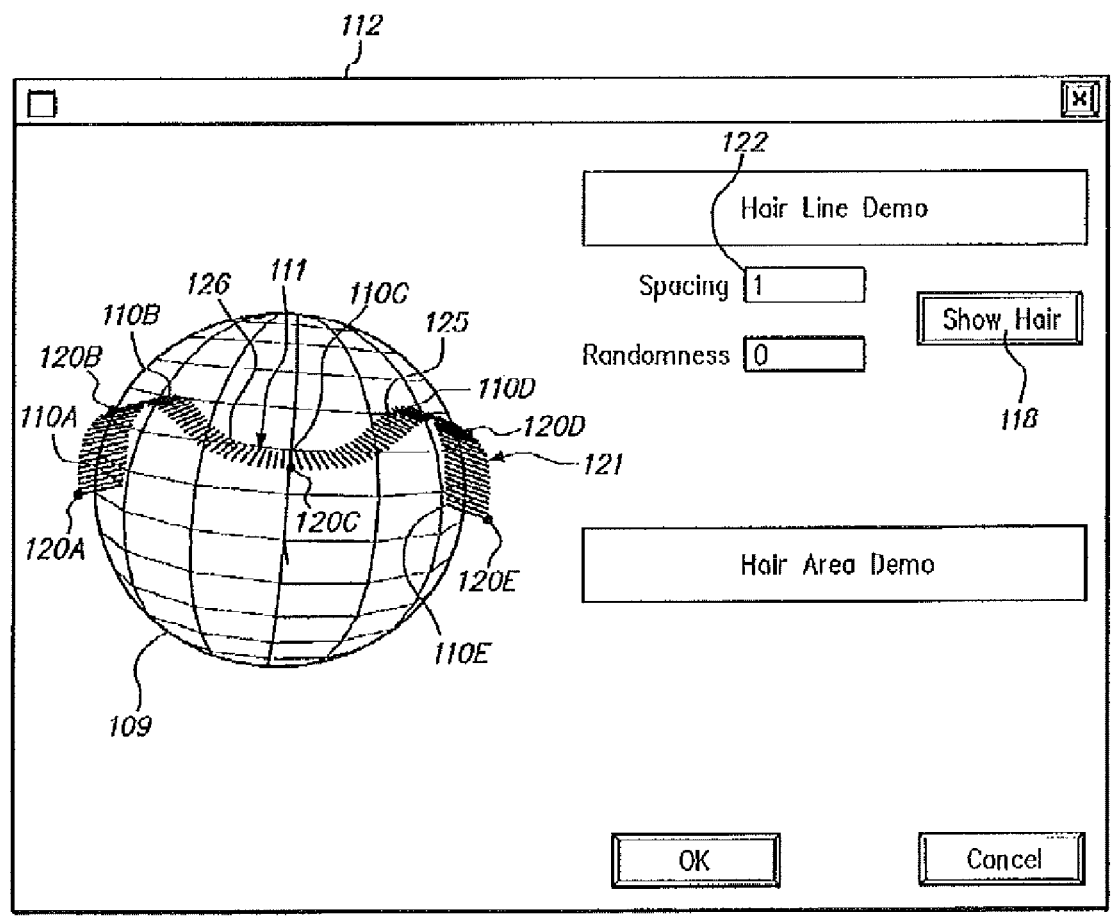
FIG. 13 is a further monitor screen shot depicting the rudimentary hair line of FIG. 12, and further displaying graphically rendered hair follicles extending from potential implantation locations along the boundary.

With reference to FIG. 13, once the hair line curve 111 has been designed to the user's initial satisfaction, i.e., by manipulation of, or adding to, control points 110A-110E, the actual follicular unit implantation locations along the hair line curve are then automatically determined by the planning module, given a user-specified density in spacing selection 122, with one follicular unit per every 1 mm specified in the user interface screen shot in FIG. 13. The planning system then traverses the curve 111 and places a follicular unit implantation site 126 at every 1 mm on the curve 111. Hair follicles 125 are then added along the proposed hair line 111 by selecting item 118 on the user interface 112. In the illustrated embodiment, the hair follicles 125 are initially generated by the system along a curve 121 that is based on identically spaced control points 120A-120E, that represent the distal tips of the hair follicles 125. The length of the hair follicles 125 is assumed to be uniform.

Figure 14:
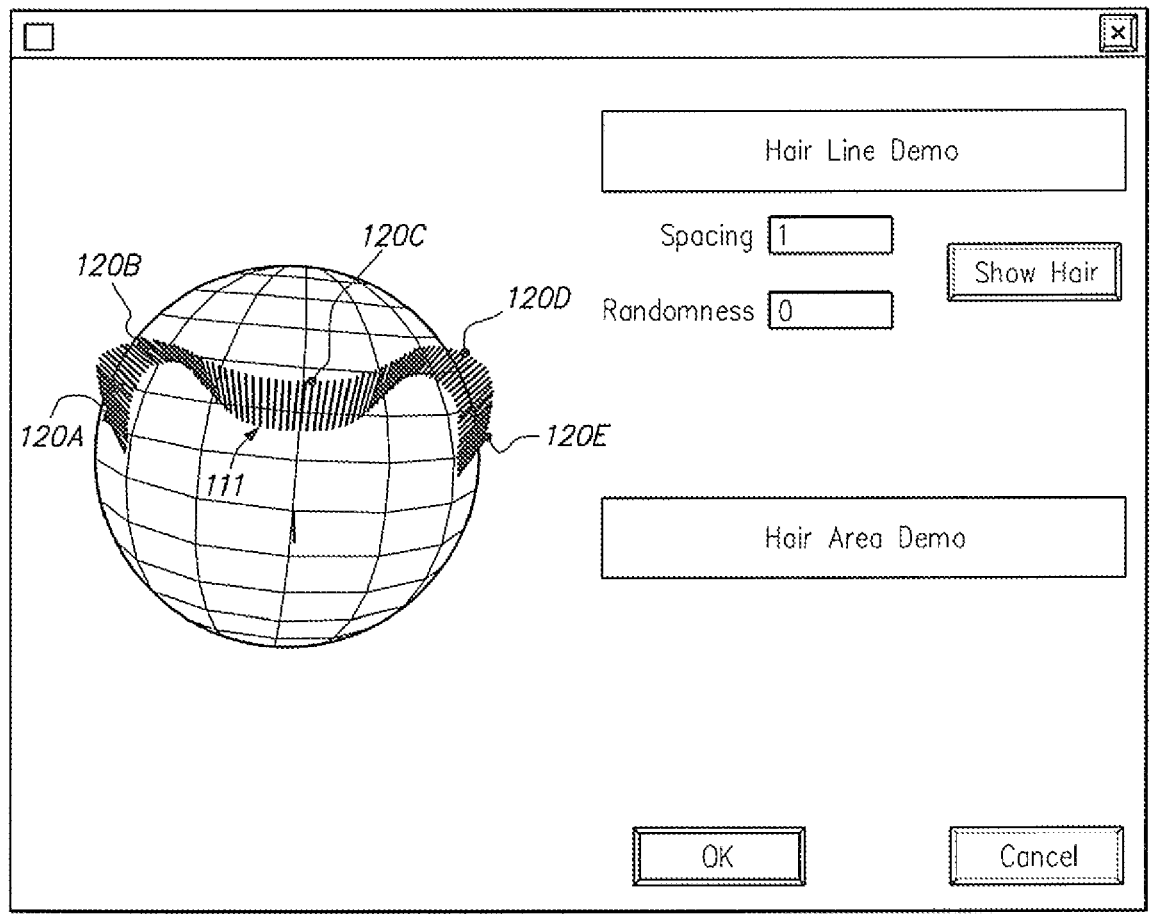
FIG. 14 is a still further monitor screen shot depicting the rudimentary hair line of FIG. 12, in which the angle(s) at which the control hair follicles displayed in FIG. 13 extend from the implantation locations have been modified.

Referring to FIG. 14, the distal tip control points 120A-120E may then be manipulated by the user to change a direction of the hair follicles, i.e., by changing the curve 121, without changing curve 111 (points 110A-110E). As will be appreciated, the change in hair follicle direction may be localized to one area of the hair line by only shifting one of the distal control points ("control directions"). Thus, by using the control directions, which are unit vectors (i.e., points on a unit sphere), one can obtain the direction of a given hair follicle 125 along the hair line 111 using the same formulation described above for the hair line implantation locations 126. The hair line direction and location together completely specify the hair line. Further hair lines may be replicated from the initial hair line, and may be added behind the initial hair line to add some thickness. The number of times the hair line is replicated may be specified by the user, within a reasonable limit. Each one of the curves can be adjusted by the user by adjusting the control points and control directions.

Figure 15:
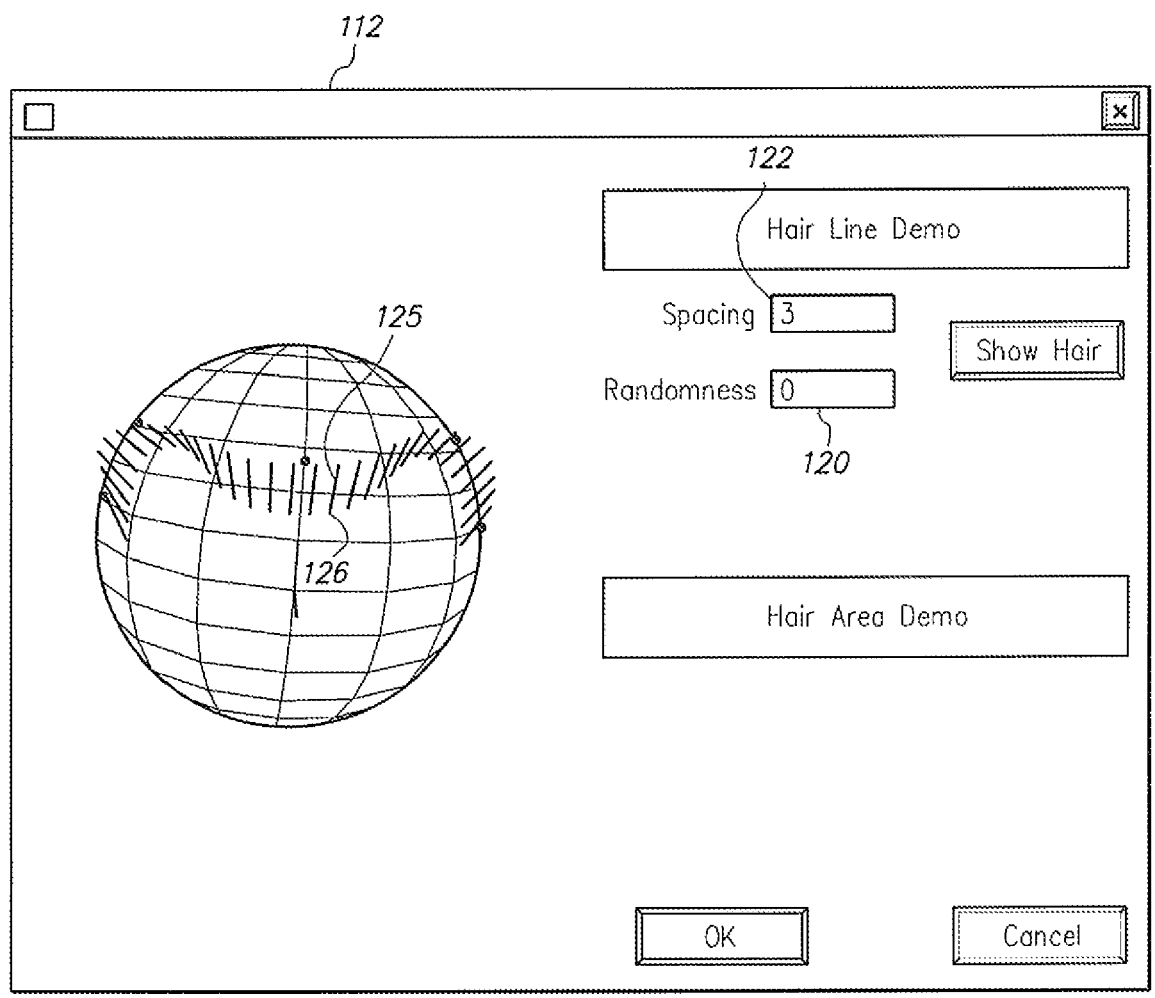
FIG. 15 is yet another monitor screen shot depicting the rudimentary hair line of FIG. 12, in which the density of the implantation locations displayed in FIG. 13 has been modified.
Figure 16:
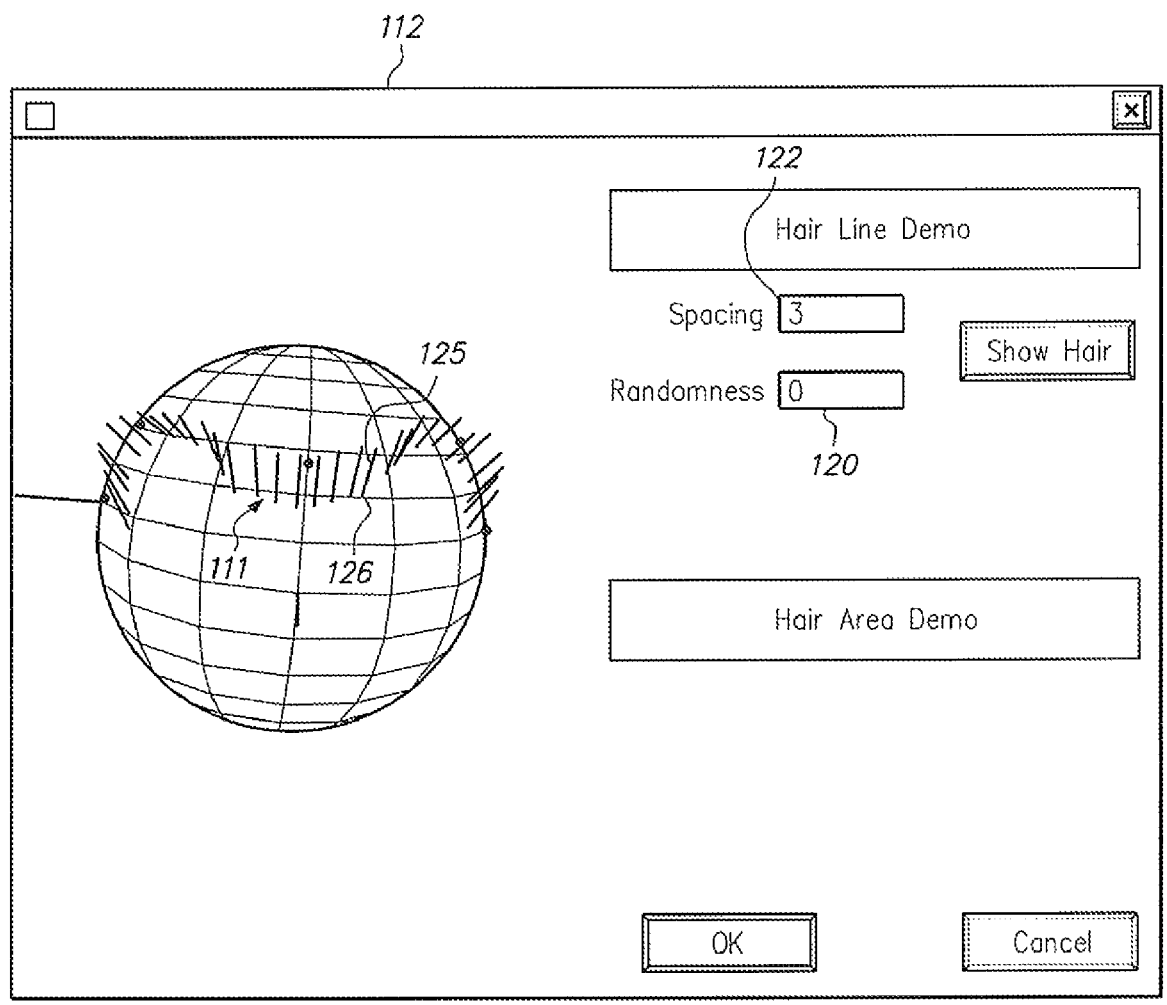
FIG. 16 is a still further monitor screen shot depicting the rudimentary hair line of FIG. 12, in which user-specified level of distribution randomness has been applied to the implantation locations displayed in FIG. 13.

FIG. 15 depicts the hair follicles 125 of the hair line curve 111, with the density (i.e., spacing input 122) of the implantation locations 126 changed from every 1 mm on the curve 111 to every 3 mm. FIG. 16 depicts the hair follicles 125 of the hair line curve 111, with the density at every 3 mm, and with the randomness 120 user-specified at 1.0 mm. In other words, each follicular unit location 126 is perturbed by 1 mm randomly, and the resulting locations are used by the planning system for the implantation sites, instead of along a uniform curve.

The hair patch design, or "Hair Area Demo" 116, is not shown but is substantially similar to that of the Hair Line Demo 114, wherein each patch is limited by a closed curve that is described by specified control points and direction(s). The hair patch is then filled, digitized, and randomized by the planning system, in accordance with user-specified density and randomness. It will also be appreciated that, in addition to graphic renderings of the patient's scalp following the implantation, the planning system will output a set of coordinates representing the specific follicular unit harvesting and implantation locations (and, in the later case, the implantation directions), which may used by an automated (e.g., robotic) hair follicular unit transplantation system, such as that described in U.S. patent application Ser. Nos. 11/380,907 and 11/421,438.

The foregoing illustrated and described embodiments of the invention are susceptible to various modifications and alternative forms, and it should be understood that the invention generally, as well as the specific embodiments described herein, are not limited to the particular forms or methods disclosed, but also cover all modifications, equivalents and alternatives falling within the scope of the appended claims. By way of non-limiting example, it will be appreciated by those skilled in the art that the planning systems and methods of their use are not limited to the use of an automated transplantation (e.g., robotic) system, and that the planning system and methods may also be used for planning transplantation procedures employing semi-automated, and manual systems and apparatus for performing the transplantation procedure.

What is claimed is:

1. A system for creating a plan for cosmetic transplantation of hair follicular units in a body surface, comprising:
    a user interface including a software-controlled processor and a user input device, wherein the processor is configured to display a three-dimensional model of the body surface, and to generate and display on the model a proposed front hair line curve, and wherein follicular unit implantation locations of the hair line curve and hair follicle orientations of the hair line curve are automatically generated based on specified control points and orientations at the control points.

2. The system of claim 1, wherein the system is configured to allow a user to interactively adjust any of the control point locations and/or orientations to thereby correspondingly adjust the proposed hair line curve.

3. The system of claim 2, wherein interactively adjusting comprises using a click and drag motion of the input device.

4. The system of claim 1, wherein control points are user selected, automatically generated, or a combination of both.

5. The system of claim 1, wherein follicular unit implantation locations and/or orientations of the hair line curve are generated from the control points using cubic interpolation techniques.

6. The system of claim 1, wherein the system is configured to allow a user to interactively adjust one or more of a respective density, direction, implant depth, degree of randomization, or overall appearance of the follicular units in the proposed follicular unit implantation locations.

7. The system of claim 1, wherein a number of the specified control points is a small fraction of the proposed follicular unit implantation locations.

8. The system of claim 1, wherein the processor is configured to determine and display on the model proposed additional follicular unit implantation locations and hair follicle orientations arranged in a configuration of one or more additional hair lines substantially replicating the front hair line curve.

9. The system of claim 8, wherein the system is configured to allow a user to specify the number of times the hair line is replicated.

10. The system of claim 1, wherein the processor is configured to generate a proposed boundary of a hair patch area based on hair patch boundary control points.

11. The system of claim 10, wherein the processor is configured to determine and display on the model proposed additional follicular unit implantation locations and hair follicle orientations within an interior of the hair patch area defined by the boundary in accordance with one or more user-specified parameters.

12. The system of claim 11, wherein any of the proposed follicular unit implantation locations and orientations are based at least in part on an attribute of existing follicular units in an identified donor area of the body surface and selected from the group comprising
    a mix of type of follicular unit,
    a quantity of each type of follicular unit,
    a relative coarseness of hair follicles growing from the follicular units,
    a direction of hair follicles growing from the follicular units,
    a color of hair follicles growing from the follicular units, and
    a randomness of the follicular units.

13. The system of claim 11, wherein the additional follicular unit implantation locations and hair follicle orientations within the interior of the hair patch area are determined at least in part based on specified hair patch control points.

14. The system of claim 1, wherein the processor is configured to display on the body surface model a proposed boundary of a donor area for harvesting follicular units, and wherein the proposed donor area boundary is originally determined, subsequently modified, or both, based on input received via the user input device.

15. The system of claim 14, wherein the proposed donor area boundary is determined based at least in part on one or more of
an amount of each of a type of existing follicular unit available for harvesting from the donor area,
an amount of each of a type of existing follicular unit to be implanted, or
a minimum density of follicular units to be left remaining in the donor area after selected harvesting of other follicular units.

16. The system of claim 1, wherein the model of the body surface further comprises additional features specific to hair follicles that are derived from the images, input through the user interface, or both.

17. A system for creating a plan for cosmetic transplantation of hair follicular units in a body surface, comprising:
a user interface including a software-controlled processor and a user input device, wherein:
the processor is configured to display a three-dimensional model of the body surface, and to generate and display on the model a proposed boundary curve having follicular unit implantation locations and hair follicle orientations, the follicular unit implantation locations and hair follicle orientations of the boundary curve are based on specified control points and orientations at the control points; and
the user interface is configured to allow a user to adjust a location and/or an orientation of at least one of the control points to cause the processor to generate and display an adjusted proposed boundary curve, wherein 1) if the location of the control point is adjusted, more than one of the follicular implantation locations is adjusted, or 2) if the orientation of the control point is adjusted, the orientation of more than one of the hair follicles is adjusted.

18. The system of claim 17, wherein the control points are user selected, automatically generated, or a combination of both.

19. The system of claim 17, wherein the hair follicle orientations and/or follicular unit implantation locations are generated from the control points using cubic interpolation techniques.

20. The system of claim 17, wherein the plan is inputted using a storage device, or a remote server.

21. The system of claim 17, wherein the processor is further configured to process images of the body surface to generate the three-dimensional model.

22. The system of claim 17, wherein the proposed follicular unit implantation locations are randomized.

23. The system of claim 17, wherein the proposed follicular unit implantation locations are calculated analytically, or obtained using a graphical construction technique.

24. The system of claim 17, wherein the proposed follicular unit implantation locations are generated using a modified interpolated curve construction.

25. The system of claim 17, wherein the processor is configured to display on the body surface model a graphic rendering of hair follicles growing from planned follicular unit implantation locations.

26. The system of claim 17, wherein at least one of the proposed follicular unit implantation locations and/or at least one of the hair follicle orientations is generated using a Bezier, Cardinal spline, or b-spline interpolation technique.

27. The system of claim 17,
wherein the user interface is further configured to display one or more input menus for receiving user inputs through the user input device for determining and adjusting the boundary curve and one or more proposed hair recipient areas.

28. The system of claim 27, wherein the one or more user-interface input menus include a hair design menu, and at least one of a hair donor menu and a hair finalize menu.

29. The system of claim 28, wherein the hair design menu is configured to receive user inputs relating to one or more of:
boundary curve planning,
hair recipient area planning, and
a user-selected request for the system to automatically generate one or both of a planned boundary curve, and a planned hair recipient area.

30. The system of claim 29, wherein the processor is configured to generate and display on the model proposed follicular unit implantation locations and hair follicle orientations based on user inputs received via respective boundary curve planning and hair recipient area planning menus.

31. The system of claim 28, wherein the hair design menu is configured to receive user inputs relating to donor area planning, including a user-selected request for the system to automatically generate a planned donor area.

32. The system of claim 27, wherein the one or more input menus comprises a hair finalize menu, the hair finalize menu is configured to receive user inputs relating to one or more of saving, transmitting, receiving and reviewing a completed or partially completed transplantation procedure plan.

33. The system of claim 27, wherein the boundary curve and/or the one or more proposed hair recipient areas are planned with respect to global landmarks.

34. The system of claim 33, wherein the global landmarks comprise existing hairs, tattoos, or other distinguishing features.

35. The system of claim 27, wherein the system is configured to determine a type of an existing follicular unit in a donor area of interest, and wherein determining and adjusting takes into consideration the determined type and/or an amount of each type of the existing follicular units in the donor area of interest.

36. The system of claim 17, wherein the proposed boundary curve comprises a front hair line.

37. The system of claim 17, wherein the proposed boundary curve comprises a boundary of a hair patch area.

38. The system of claim 17, wherein the location and/or the orientation of the at least one of the control points is adjusted by using a click and drag motion of the input device.

39. The system of claim 17, wherein the processor is configured to determine additional proposed follicular unit implantation locations and hair follicle orientations in one or more hair recipient areas.

40. The system of claim 39, wherein the system is configured to allow the user to interactively adjust one or more of a respective density, direction, implant depth, degree of randomization, or overall appearance of the follicular units in any of the proposed follicular unit implantation locations.

* * * * *